Aug. 26, 1975 J. C. MIKKELSEN Plant Pat. 3,772
BEGONIA PLANT
Filed July 10, 1974
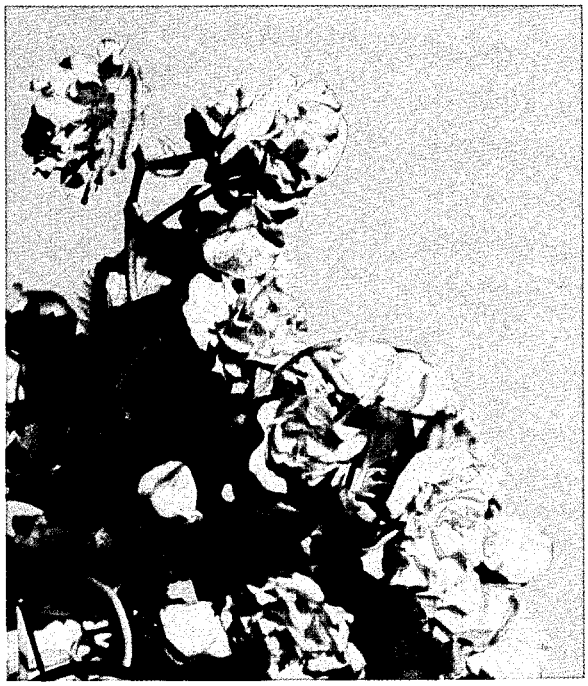

United States Patent

Plant Pat. 3,772
Patented Aug. 26, 1975

3,772

BEGONIA PLANT

James C. Mikkelsen, Ashtabula, Ohio, assignor to Mikkelsens Inc., Ashtabula, Ohio

Filed July 10, 1974, Ser. No. 487,398
Int. Cl. A01h *5/00*
U.S. Cl. Plt.—68 1 Claim

The present invention relates to a new and distinctive variety of begonia plant, botanically known as *Begonia elatior,* (B × *hiemalis*—Fotsch), discovered by me as a flowering mutation of Aphrodite Rose (not patented). Asexual reproduction by stem cuttings has reproduced the unique features of the new variety through successive propagations.

The following characteristics distinguish the new begonia from both its parent and other begonias commercially known and used in the floriculture industry:

1. Flowers having a more distinctive rose pink color considerably lighter in shade then the parent cultivar.
2. Edges of the tepals are clearly ruffled and are consistently so regardless of the time of flowering.
3. More tendency to being procumbent adding additional flexibility to the stems for use in hanging baskets.
4. Leaf cutting propagation is inconsistent necessitating propagation by stem cuttings.
5. Like its parent, the new variety is quite resistant to powdery mildew.
6. To date no evidence of reproductive organs—must assume that like its parent it is a sterile triploid.
7. Flowers are double azalea type.
8. Rate of growth is faster than other Rieger Aphrodite varieties except Aphrodite Rose, its parent. Greater expression of self-branching. Increased self-branching is of economic benefit to growers and propagators as there is a faster plant build-up.

The accompanying colored photographic drawing is a close-up photograph of the new variety, showing the color as true as reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

*Parentage*: Mutation of Rieger's Aphrodite Rose.

*Propagation*: Propagates from stem cuttings in four to five weeks in 2" plastic pots at 20°–21° C. Leaf cuttings will root in same period of time but are too inconsistent in producing adventitious shoots.

*Rooting Habit*: Quite rapid, well textured, dentritic, uniform initiation around base of cutting.

*Form*: Low, sprawling. Needs support if grown as an upright specimen. Best grown in hanging basket type container.

*Habit of Growth*: Procumbent, self-branching, rapid plant development.

*Blooming Habits*: Ideal environment for blooming is eleven to twelve hour day length at 17°–18° C. Once flowering has initiated, continuous flowering has been observed for six months.

*Blooming Season*: Normal season would be in November. Flowering can be manipulated by controlling the environment with modern production practices.

*Foliage*: Oval to nearly round, with some slight serration, little if any sinus depth. Highly glossy/reflective. Crisp texture.

- *Size*—Eight to ten cm. in diameter.
- *Shape*—Oval to round.
- *Texture*—Firm and crisp.
- *Margin*—Almost complete—slight serration.
- *Color*—Old leaf—top 147A, under 148A. New leaf—top 146A, under 148A.

*Disease Resistance*: Very resistant to powdery mildew compared to other begonias grown under same conditions. More resistant than Rieger's Schwabenland types.

*Flowers*:

- *Borne*—On trusses usually in alternating positions on the stem. Will sun scald if in direct summer sunlight at temperatures above 25°–28° C. Five to six cm. in diameter.
- *Quantity*—Flowering abundance is equal to parent variety; quite profuse as indicated in the drawing.
- *Buds*—Typical of these begonias—flat, size of small coin (dime) before beginning to open. Flower retention is good to excellent.
- *Tepals*—Ruffled numbering eight to ten—good doubleness. Color between 54B when opening to 52B at maturity.

*Reproductive Organs*:

- *Stamens*—None seen.
- *Pollen*—None seen.
- *Styles/Ovaries*—None seen.

I claim:

1. A new and distinct cultivar of begonia plant characterized particularly by its distinctive rose pink flower color; its ruffled edged tepals which are consistently so shaped regardless of the time of flowering; its tendency to be procumbent thereby providing additional flexibility to the stems for use in hanging baskets and by its inconsistent propagation by leaf cuttings thereby necessitating propagation by stem cuttings.

No references cited.

ROBERT E. BAGWILL, Primary Examiner